US00PP08578P

United States Patent [19]

Warriner, deceased

[11] Patent Number: Plant 8,578

[45] Date of Patent: Feb. 8, 1994

[54] MINIATURE ROSE PLANT NAMED 'JACMO'

[75] Inventor: William A. Warriner, deceased, late of Tustin, Calif. by Alene B. Warriner, legal representative

[73] Assignee: Bear Creek Gardens, Inc., Medford, Oreg.

[21] Appl. No.: 952,962

[22] Filed: Sep. 28, 1992

[51] Int. Cl.[5] ..... A01H 5/00

[52] U.S. Cl. ..... Plt./10.1

[58] Field of Search ..... Plt. 7.1, 10.1

*Primary Examiner*—Howard J. Locker

*Attorney, Agent, or Firm*—Klarquist, Sparkman, Campbell, Leigh and Whinston

[57] ABSTRACT

A miniature rose plant having bright orange flowers, appendages on all of its sepals, a compact plant habit and an ease of propagation by softwood cuttings.

1 Drawing Sheet

The present invention relates to a new and distinct variety of rose plant of the miniature class which was originated by the inventor by crossing the variety Chattem Centennial, U.S. Plant Pat. No. 4,564, with the variety KORp, U.S. Plant Pat. No. 3,380.

The primary objective of this breeding was to produce a new rose variety having compact plant habit of the female parent combined with the bright orange flower color of the male parent. The objective was substantially achieved along with other desirable improvements as evidenced by the following unique combination of characteristics which are outstanding in the new variety and which distinguish it from its parents, as well as from all other varieties of which I am aware:

1. Bright orange with light orange reverse petals;
2. Compact vigorous plant;
3. Appendages on all sepals; and
4. Propagates easily from softwood cuttings.

Asexual reproduction of this new variety by softwood cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Chattem Centennial, U.S. Plant Pat. No. 4,564.

*Pollen parent.*—KORp, U.S. Plant Pat. No. 3,380.

Classification:

*Botanical.*—Rosa hybrida.

*Commercial.*—Miniature.

FLOWER

Observations made from specimens grown in a garden environment in Somis, Calif., from March through July, 1992.

Blooming habit: Recurrent.

Bud:

*Size.*—¾ inch when the petals start to unfurl.

*Form.*—Short, pointed ovoid.

*Color.*—When sepals first divide, bud color is Orange Red Group 30A with the lower ¼ of the bud near Yellow Group 12B. When half blown, the upper sides of the petals are Orange Red Group 30A; and the lower sides of the petals are Orange Red Group 29A with the lower ⅓ of the petals yellow Group 12B to C.

*Sepals.*—Color: Green Group 138A. Surface texture: Covered in fine hairs. There are three heavily appendaged sepals. There are two sepals with some appendages and hairy edges.

*Receptacle.*—Color: Green Group 138A. Shape: Funnel. Size: Small (⅛×⅛ inch). Surface: Smooth.

*Peduncle.*—Length: Short (¾ inch). Surface: Glandular. Color: Medium green and bronzy where exposed to the sun. Strength: Stiff, erect.

Bloom:

*Size.*—Small. Average open size is 1½ inches.

*Borne.*—Singly and several (usually 3 to 7) together. If in clusters: Pyramidal.

Stems.—Short (4 to 6 inches).

Form.—When first open: High centered. Permanence: Flattens, outer petals curl back.

*Petalage.*—Number of petals under normal conditions: 25.

Color.—The upper side of the petals is Red Orange Group 30A. The reverse side of the petals is Red orange Group 29A with the lower ⅓ of the petal Yellow Group 12B to C. The bases of the petals are Yellow Group 12A. The major color on the upper side is Red Orange Group 30A.

*Variegations.*—None.

*Discoloration.*—No change in the general tonality at the end of the first day or at the end of the third day.

*Fragrance.*—Slight.

Petals:

*Texture.*—Thin.

*Shape.*—Deltoid.

*Form.*—Tips slightly recurved, edges slightly quilled.

*Arrangement.*—Imbricated, with no petaloids in the center.

*Persistence.*—Drop off cleanly.

*Lastingness.*—On the plant: Short (3 to 4 days). As a cut flower: Short (5 days).

Reproductive parts:

*Anthers.*—Size: Medium. Quantity: Many. Color: Reddish brown. Arrangement: Regular around styles.

*Filaments.*—Color: Yellow.

*Pollen.*—Color: Gold yellow.

*Styles.*—Color: Red.

*Stigmas.*—Color: Yellow.

Form: Bush.

Growth: Vigorous, dwarf, upright, branching.

Average plant height is around 30 inches. Foliage: Number of leaflets on normal mid-stem leaves: 5 or 7.

*Size.*—Small ($2\frac{1}{4} \times 1\frac{1}{2}$ inches).

*Quantity.*—Abundant.

*Color* .—New foliage: Reddish. Old foliage: Dark green.

Leaflets:

*Shape.*—Pointed oval.

*Texture.*—Upper side: Smooth and semi-glossy.

*Edge.*—Serrated.

*Serration.*—Single, small.

*Petiole rachis.*—Color: Reddish.

*Petiole underside.*—Smooth, with occasional prickles.

Stipules.—Short, serrated.

*Disease resistance.*—Susecptible midlew, but resistant to rust under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base and on laterals from main canes: Ordinary.

*Form.*—Short ($\frac{3}{8}$ inch), hooked slightly downward.

*Color when young.*—Red.

Small prickles:

*Quantity.*—On main stalks and on laterals: Few.

*Color*—Brown.

I claim:

1. A new and distinct variety of rose plant of the miniature class, substantially as herein shown and described, characterized particularly as to novelty by the unique combination of its bright orange flowers, by having appendages on all of its sepals, by its compact plant habit and its ease of propagation by softwood cuttings.

* * * * *

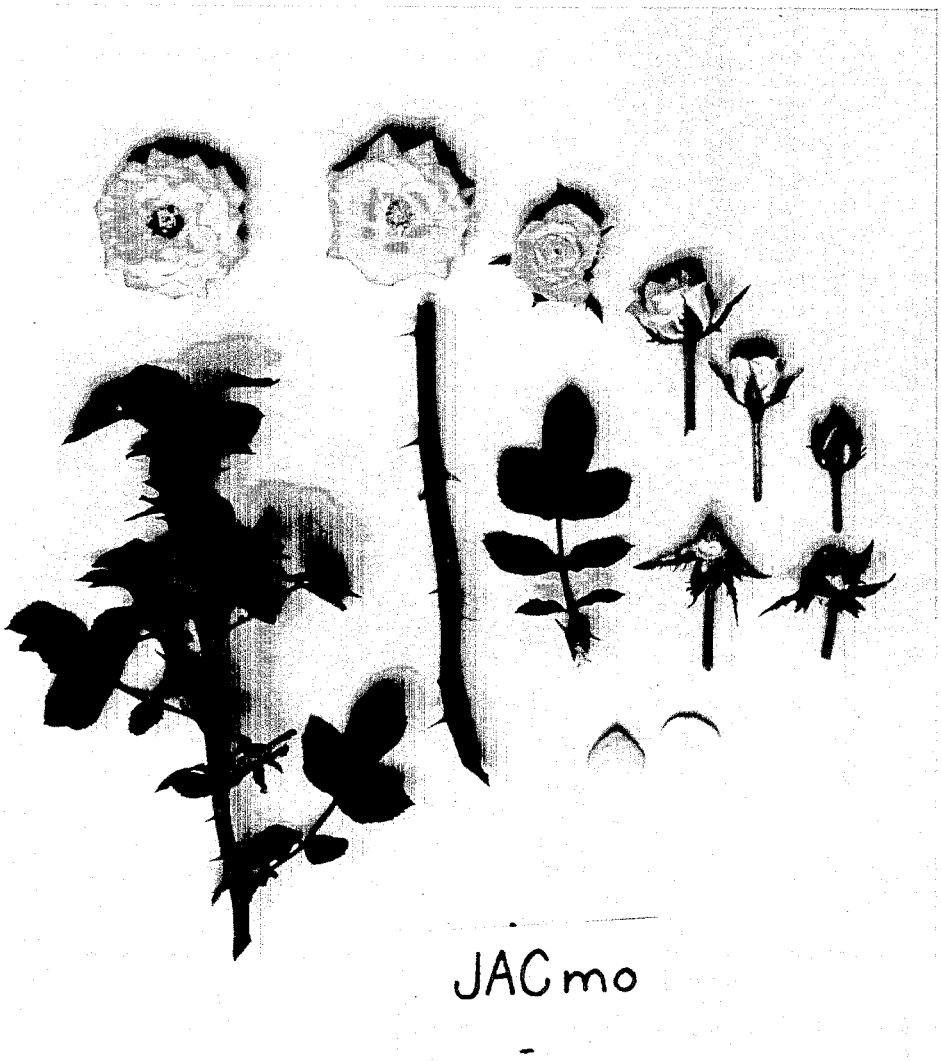
JACmo